United States Patent [19]

Morabito et al.

[11] Patent Number: 5,001,071
[45] Date of Patent: Mar. 19, 1991

[54] VENTED RETENTION GAP CAPILLARY GAS CHROMATOGRAPHY METHOD

[75] Inventors: Paul L. Morabito; Joseph F. Hiller; Terrence McCabe; Thomas L. Peters, all of Midland, Mich.

[73] Assignee: The Dow Chemical Company, Midland, Mich.

[21] Appl. No.: 254,538

[22] Filed: Oct. 6, 1988

[51] Int. Cl.[5] ............................................. G01N 30/02
[52] U.S. Cl. ...................................... 436/161; 422/89; 55/67
[58] Field of Search ...................... 55/197, 67; 422/89; 436/161

[56] References Cited

U.S. PATENT DOCUMENTS 3,285,701 11/1966 Robertson .......................... 422/89 X
4,935,145 6/1990 Cortes et al. ...................... 436/161 X

OTHER PUBLICATIONS

K. Grob, Jr. et al., *Journal of Chromatography*, 334, pp. 129-155 (1985).
G. Schomburg et al., *Journal of High Resolution Chromatography & Chromatography Comm.*, 5, pp. 565-567 (Oct. 1982).
A. Farbrot Buskhe et al., *Journal of High Resolution Chromatography & Chromatography Comm.*, 11, pp. 16-20 (Jan. 1988).
Th. Noy et al., *Journal of High Resolution Chromatography & Chromatography Comm.*, 11, pp. 181-186 (Feb. 1988).
K. Grob et al., *Journal of High Resolution Chromatography & Chromatography Comm.*, 11, pp. 388-394 (May 1988).

Primary Examiner—Charles Hart
Attorney, Agent, or Firm—Timothy S. Stevens

[57] ABSTRACT

A method for on-column injection of large sample volumes using the retention gap technique in capillary gas chromatography for sample components of interest that would be obscured by the large solvent peak otherwise inherent in the technique. This interference from the large solvent peak is removed by venting carrier flow from the retention gap to waste for a limited time, long enough to discard much of the solvent without serious loss of the sample component of interest.

12 Claims, 1 Drawing Sheet

VENTED RETENTION GAP CAPILLARY GAS CHROMATOGRAPHY METHOD

FIELD OF THE INVENTION

The invention is in the field of capillary gas chromatography and more particularly is in the field of on-column injection capillary gas chromatography systems using a retention gap.

BACKGROUND OF THE INVENTION

Capillary gas chromatography is one of the most important methods used for chemical analyses. There will probably always be a desire to improve the sensitivity and selectivity of capillary gas chromatography. Capillary gas chromatography was advanced by the use of a retention gap, i.e., a section of capillary tubing preceding the column that is deactivated but not coated with a stationary phase. It is possible to inject a relatively large volume of a liquid sample on-column directly into the retention gap so that a component of the sample can be chromatographed with increased sensitivity. However, when this is done the sample solvent peak is very large and tends to overlap and obscure peaks that correspond to sample components that otherwise are only slightly more retained than the solvent of the sample even though the slightly more retained peaks then elute at a longer retention time.

Noy et al., *Journal of High Resolution Chromatography & Chromatography Communications*, February 1988, (181-186), disclosed venting away to waste most of the injected sample solvent (hexane) between a cold trap (incorporating an uncoated section of capillary tubing) and a capillary gas chromatography column. However, when this was done there was a significant reduction of recovery for the sample components of interest more volatile than C20 hydrocarbon (C10-C26 hydrocarbons were tested) and with essentially complete loss of C10 hydrocarbon. There is a need for an on-column injection capillary gas chromatography system using a retention gap for injecting very large volumes of samples containing sample components of interest that are only slightly less volatile than the solvent of the sample.

SUMMARY OF THE INVENTION

The present invention is a gas chromatographic method suitable for the injection of large volumes of a sample containing a volatile solvent and a slightly less volatile component of interest. The method comprises five steps and solves the above-stated problem of the prior methods. The first step is to flow a stream of carrier gas through a retention gap. The next step is to inject a preselected volume of the sample into the retention gap. The boiling point of the component of interest must be less than 100° C. higher than the boiling point of the solvent of the sample. The third step is to selectively vaporize the injected sample into the stream of carrier gas flowing through the retention gap so that vaporized sample emerges from the retention gap in the stream of carrier gas flowing through the retention gap initially enriched with the solvent and finally enriched with the component of interest. The fourth step is to vent to waste for a period of time at least one-half of the stream of carrier gas emerging from the retention gap enriched with the sample solvent. The period of time is less than that time needed to transport more than one-half of the component of interest through the retention gap and is more than that time needed to transport one-half of the sample solvent through the retention gap. The last step is to flow at least one-quarter of the stream of carrier gas emerging from the retention gap into a capillary gas chromatography column for a period of time needed to transport at least one-eighth of the component of interest from the retention gap into the gas chromatography column.

DETAILED DESCRIPTION OF THE INVENTION

Figure 1:
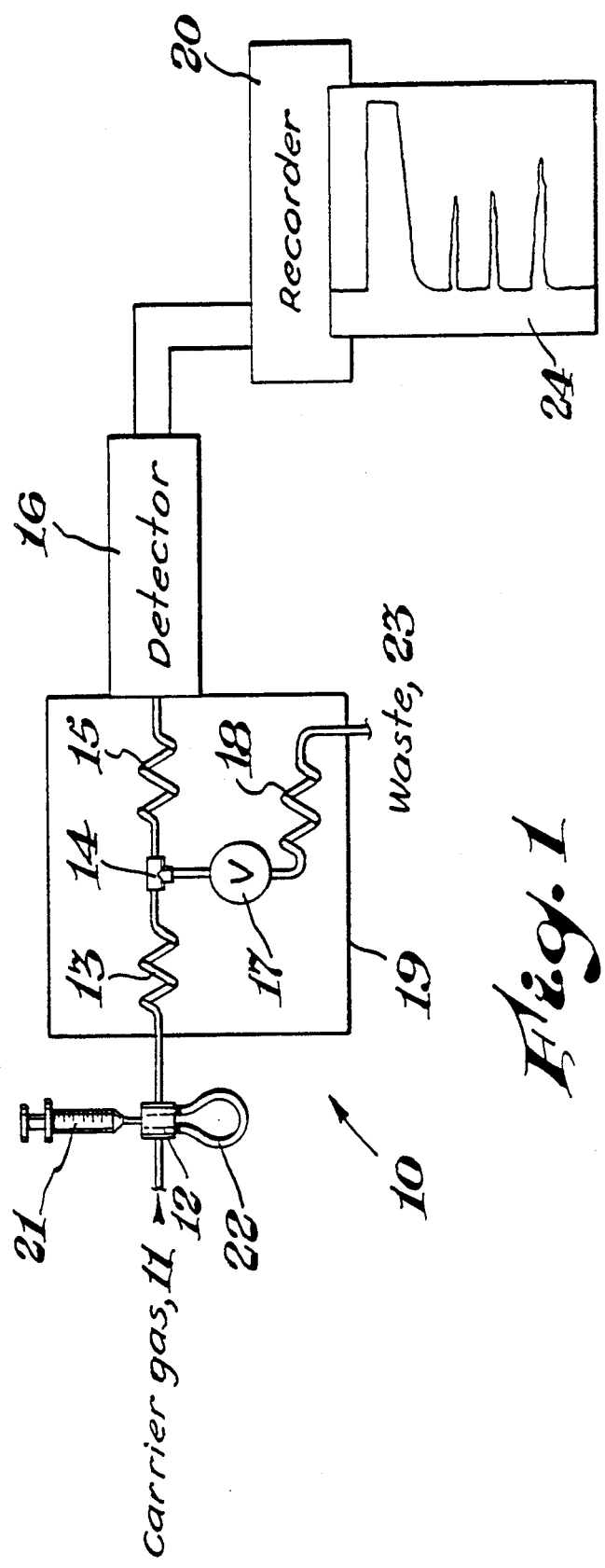
FIG. 1 is a schematic drawing of an apparatus that can be used to practice the method of the present invention.

Referring now to FIG. 1, therein is shown a schematic drawing of a gas chromatography system 10 suitable for performing the present method. The system 10 includes a supply of carrier gas 11 such as helium. The carrier gas 11 is flowed through a loop-type injection valve 12, a retention gap 13, a tee 14, a capillary gas chromatography column 15 and then to a detector 16. The tee 14 is also connected to an on-off valve 17. A coil of capillary tubing 18 is also connected to the valve 17. The retention gap 13, tee 14, column 15, valve 17, and tubing 18 are all contained in an oven 19 of a gas chromatograph. A strip-chart recorder 20 is connected to the detector 16 for recording chromatograms. The system 10 is but one apparatus that can be used in the present invention and many variations in apparatus can be made.

The present invention is suitable for the injection of relatively large volumes, e.g., more than 10 $\mu l$ and typically 100-500 $\mu l$, of liquid sample, the sample containing a volatile solvent such as hexane and a less volatile component of interest such as heptane. Relative volatility between two compounds in solution is a complex subject. For example, if one compound is polar (for example, water or methanol) and the other is relatively non-polar (for example, heptane), then relative volatility may have less correlation with the atmospheric pressure boiling points of the compounds in question than if both compounds are non-polar (for example, hexane and heptane). On the other hand, atmospheric pressure boiling points are easily ascertained and for non-polar compounds at least, correlate reasonably well with volatility. Therefore, the bounds of the present invention have been drawn to include the limitation that the sample component of interest have an atmospheric pressure boiling point of less than 100° C. or 50° C. or 25° C. higher than the atmospheric pressure boiling point of the solvent of the sample. In most gas chromatography applications, there are a number of sample components of interest and in the present invention at least one of them must meet the above stated relative boiling point test.

Referring again to FIG. 1, the sample is initially contained in a syringe 21 which is used to fill a tubing loop 22 connected at each end thereof with the injection valve 12. Loop-type injection valves, such as the valve 12, are more frequently used in liquid chromatography than in gas chromatography but are also well understood by the gas chromatography art. Preferably, the volume of the loop 22 is at least 10 $\mu l$ for the invention at its present state of development because if less than 1.0 $\mu l$, then sample carryover problems can become significant. However, it should be understood that the present invention is not intended to be limited to injections of more than 10 μl. It is believed, however, that for many applications, the present invention provides maximum benefit in detecting and quantifying very low concentrations of such components of interest in a sample by injecting as much as 200–500 μl or more without the chromatographic peak for the component of interest being overlapped and obscured by the solvent peak.

When the valve 12 is actuated, a preselected volume of the sample in the loop 22 is injected into the retention gap 13 by the flow of the carrier gas 11. The sample undergoes a selective vaporization in the retention gap 13 into the carrier gas 11. The exact mechanism of operation of such a retention gap is not known at this time but Grob et al., *Journal of Chromatography*, 334, (1985) 129–155, offers one explanation. In an overall sense, :f the sample is substantially and selectively vaporized into the carrier gas 11 so that it emerges from the retention gap 13 initially enriched with the solvent and finally enriched with the component of interest (relative to the fraction of each in the original sample), then one step of the present method has been met.

The stream of carrier gas 11 flowing from the retention gap 13 is flowed to the tee 14. The tee 14 is connected to both the column 15 and the valve/tubing 17/18. If the valve 17 is open, then the stream of carrier gas 11 flowing from the retention gap 13 is split with a portion flowing through the column 15 and a portion flowing to waste 23. The ratio of these two flows is determined by the resistance to flow of the two paths and in the present invention at least one-half of the stream of carrier gas 11 emerging from the retention gap 13 when it is so enriched with the solvent must flow to waste 23. For this to happen, the valve 17 must be in the on or open position. If the tubing 18 is relatively short in length and/or has a relatively large internal diameter, then the ratio of carrier gas 11 flowing to waste 23 will be that much greater. The timing of operation of the valve 17, or its equivalent, is critical in the present invention. Typically, the valve 17 is turned on before the injection valve 12 is actuated to inject a sample and is left on for a period of time less than the period of time needed to transport more than one-half of the component of interest of the injected sample through the retention gap 13 and greater than the period of time needed to transport one-half of the solvent of the injected sample through the retention gap 13. This step of the present invention insures that at least one-half of the injected solvent is not eventually seen by the detector 16 and does not contribute to overloading of the column 15.

Then, in a preferred embodiment, the valve 17 is turned off so that substantially all of the carrier gas 11 emerging from the retention gap 13 flows through the column 15. Critically, at least one quarter of this stream of carrier gas 11 flowing from the retention gap 13 must go into the column 15 for a period of time needed to transport at least one-eighth of the component of interest of the injected sample from the retention gap into the column 15. This step of the present invention insures that a critical minimum amount of the injected component of interest is put into the column 15 and below this amount the present method is not believed to be beneficial. It should be understood that the valve/tubing 17/18 is but one apparatus means for carrying out the present method and that the valve 17 can be a three-way valve with no off state, e.g., venting most of the flow of carrier gas 11 to waste at first and then relatively little to waste.

Most preferably, and preferably at least nine-tenths and at least three-quarters, respectively, of the stream of carrier gas emerging from the retention gap 13 enriched with the solvent of the injected sample is flowed to waste 23 for the first period of time mentioned. Most preferably, the first period of time is less than the period of time needed to transport more than one-quarter of the component of interest of the injected sample through the retention gap 13 and is greater than the period of time needed to transport three-quarters of the solvent of the injected sample through the retention gap 13. Most preferably, more preferable and preferably at least nine-tenths, at least three-quarters and at least one-half, respectively, of the stream of carrier gas flowing from the retention gap 13 is flowed into the column 15 for the second mentioned period of time needed to transport at least two-thirds, at least one-third and at least one-quarter, respectively, of the component of interest of the injected sample into the column 15.

The continuing flow of carrier gas 11 through the column 15 results in the component of interest eventually emerging from the column 15 to be detected by the detector 16. Over time, after injection, the recorder 20 thus traces a chromatograms 24 as is well understood in the art.

Preferably, the valve 17 is automatically actuated a set time after the injection valve 12 is actuated to inject a sample. This can be done using the timed event function of many recording integrators, by computer control, and even by a time controller, to name a few of the many possible means available to the art at this time. The time delay between actuation of valve 12 and valve 17 is critical in the invention, as discussed in detail above, and can probably be quantitatively determined by analyzing the flow stream at the tee 14 over time. However, it is believed to be simpler and easier to determine the recovery of the most volatile component of interest as a function of the timing of the activation of the valve 17. If the valve 17 is left in the on position too long, then the chromatogram 24 will show a relatively small solvent peak but the percent recovery of the component of interest will be minimal because the component of interest will have been vented to waste. If the valve 17 is switched to the off position too early, then the chromatogram 24 will show a relatively large solvent peak that will overlap with the peak from the component of interest. By a procedure of limited trial and error experiments it is possible to determine a reasonably optimum time for the activation of the valve 17.

The percent recovery of the component of interest can be determined as follows. Inject the same amount of the component of interest in a very much smaller volume of sample and leave the valve 17 in the off position during the whole analysis. If the volume of sample is low enough, separate solvent and component of interest peaks will be seen. The area of the component of interest peak is then measured and compared on a percent basis to the area of the component of interest peak when using the method of the present invention. The percent recovery is most preferably at least about 66% and critically is at least about 13%.

EXAMPLE 1

A system generally similar to that shown in FIG. 1 is assembled. A Hewlett Packard 5890 gas chromatograph having a flame ionization detector 16 is modified by attaching it to an automatically activated Valco N6W loop type sample injector valve 12. Instead of the syringe 21, a Micromerities Model 725 auto injector is connected to the valve 12 (with the injection valve supplied with the autosample left electrically connected to the autosampler but not used). The retention gap 13 is a 30-meter long, 0.53 mm internal diameter Restek phenyl-methyl siloxane deactivated fused silica capillary tube. The column 15 is a 30-meter long, 0.32 mm internal Restek Rt-5, 1 $\mu$m film coating, fused silica capillary column. The tee 14 is a Hewlett Packard Press Fit catalog no. 5041-2179. The retention gap 13 is connected to the tee 14 by a 0.53 to 0.32 mm Hewlett Packard Press Fit union and a short piece of 0.32 mm internal diameter deactivated fused silica tubing. The valve 17 is a SGE micro-pneumatic automatic on-off valve MOVP-1/100 in its "L" configuration. A Nelson Analytical 6000 Systems integrator recorder 20 is used to generate the chromatograms 24 and to control the valves 17 and 12 via a Nelson digital control module and interface. The tubing 18 is a 30 cm long length of 0.32 mm internal diameter fused silica capillary. It is useful to add a small amount of polyimide to the back of the Press Fit connectors to provide mechanical stability until they have been heated in the oven 19 of the gas chromatograph. The loop 22 is a 100 $\mu$l internal volume length of Teflon tubing. However, the retention gap 13 is long enough for at least a 250 $\mu$l volume loop 22. The valve 17 is programmed to be on until 2.25 minutes after the injection valve 12 is actuated to inject. The length of the retention gap 13 outside the oven 19 is as short as possible since this length is not heated.

The gas chromatograph is set for a 100° C. injector temperature (the retention gap 13 is routed through the gas chromatograph's injector port), a 250° C. detector temperature, an oven 19 program of 65° C. for 7 minutes and then an 8° C. per minute program to 300° C. with a 3 minute hold at 300° C. The carrier gas is helium and the column flow rate is 1.8 ml per minute with the valve 17 off and 0.7 ml per minute with the valve 17 on or open to waste 23. The retention gap 13 flow rate is 1.8 ml per minute with the valve 17 off and 20 ml per minute with the valve 17 on. The detector 16 requires make-up gas which is nitrogen at 25 ml per minute. It is noticed that the valve 17 has a small leak rate when in the off position and this is believed to be probably beneficial in reducing solvent peak tailing but this is not known.

EXAMPLE 2

The system of Example 1 is used to analyze replicate injections of a sample of hexane (C-6) containing: 1.84 $\mu$g of n-heptane (C-7) per ml; 1.85 $\mu$g of isooctane (C-8) per ml; 1.96 $\mu$g of n-nonane (C-9) per ml; and, 1.92 $\mu$g of n-decane (C-10) per ml. The chromatograms from each injection show baseline separation of all peaks, no obscuring of the n-heptane peak by the hexane peak, and average recoverys of 70%, 62%, 99% and 101%, respectively for the C-8, C-7, C-9 and C-10 peaks with respective relative standard deviations of peak area of about 8.5%, 0.7%, 0.5% and 0.5%.

What is claimed is:

1. A gas chromatographic method suitable for injection of large volumes of sample, the method comprising the steps of:
   (a) flowing a stream of carrier gas through a retention gap;
   (b) injecting a preselected volume of a sample into the retention gap, the sample comprising a volatile solvent and a less volatile component of interest having a boiling point at atmospheric pressure of less than 100° C. higher than the boiling point of the solvent at atmospheric pressure;
   (c) selectively vaporizing the injected sample into the stream of carrier gas flowing through the retention gap so that vaporized sample emerges from the retention gap in the stream of carrier gas flowing through the retention gap initially enriched with the volatile solvent of the injected sample and finally enriched with the less volatile component of interest of the injected sample;
   (d) flowing at least one-half of the stream of carrier gas emerging from the retention gap enriched with the volatile solvent of the injected sample to waste for a first period of time, the first period of time being less than the period of time needed to transport more than one-half of the component of interest of the injected sample through the retention gap and being greater than the period of time needed to transport one-half of the solvent of the injected sample through the retention gap;
   (e) then, flowing at least one-quarter of the stream of capillary gas chromatograph column for a second period of time needed to transport at least one-eighth of the component of interest of the injected sample from the retention gap into the gas chromatography column.

2. The method of claim 1 wherein in step (d) at least three-quarters of the stream of carrier gas emerging from the retention gap enriched with the volatile solvent of the injected sample is flowed to waste for a first period of time, the first period of time being less than the period of time needed to transport more than one-half of the component of interest of the injected sample through the retention gap and being greater than the period of time needed to transport one-half of the solvent of the injected sample through the retention gap and wherein in step (e) at least one-half of the stream of carrier gas emerging from the retention gap is flowed into the gas chromatography column for a second period of time needed to transport at least one-quarter of the component of interest of the injected sample from the retention gap into the gas chromatography column.

3. The method of claim 1 wherein in step (d) at least about nine-tenths of the stream of carrier gas emerging from the retention gap enriched with the volatile solvent of the injected sample is flowed to waste for a first period of time, the first period of time being less than the period of time needed to transport more than one-half of the component of interest of the injected sample through the retention gap and being greater than the period of time needed to transport one-half of the solvent of the injected sample through the retention gap and wherein in step (e) at least three-quarters of the stream of carrier gas emerging from the retention gap is flowed into the gas chromatography column for a second period of time needed to transport at least one-third of the component of interest of the injected sample from the retention gap into the gas chromatography column.

4. The method of claim 1 where in step (d) at least nine-tenths of the stream of carrier gas emerging from the retention gap enriched with the volatile solvent of the injected sample is flowed to waste for a first period of time, the first period of time being less than the period of time needed to transport more than one-quarter of the component of interest of the injected sample through the retention gap and being greater than the period of time needed to transport three-quarters of the solvent of the injected sample through the retention gap and wherein in step (e) at least about nine-tenths of the stream of carrier gas emerging from the retention gap is flowed into the gas chromatography column for a second of time needed to transport at least two-thirds of the component of interest of the injected sample from the retention gap into the gas chromatography column.

5. The method of claim 1 wherein in step (b) the atmospheric pressure boiling point of the component of interest is less than 50° C. higher than the atmospheric pressure boiling point of the solvent.

6. The method of claim 5 wherein in step (d) at least three-quarters of the stream of carrier gas emerging from the retention gas enriched with the volatile solvent of the injected sample is flowed to waste for a first period of time, the first period of time being less than the period of time needed to transport more than one-half of the component of interest of the injected sample through the retention gap and being greater than the period of time needed to transport one-half of the solvent of the injected sample through the retention gap and wherein in step (e) at least one-half of the stream of carrier gas emerging from the retention gap is flowed into the gas chromatography column for a second period of time needed to transport at least one-quarter of the component of interest of the injected sample from the retention gap into the gas chromatography column.

7. The method of claim 5 wherein in step (d) at least nine-tenths of the stream of carrier gas emerging from the retention gap enriched with the volatile solvent of the injected sample is flowed to waste for a first period of time, the first period of time being less than the period of time needed to transport more than one-half of the component of interest of the injected sample through the retention gap and being greater than the period of time needed to transport one-half of the solvent of the injected sample through the retention gap and wherein in step (e) at least three-quarters of the stream of carrier gas emerging from the retention gap is flowed into the gas chromatography column for a second period of time needed to transport at least one-third of the component of interest of the injected sample from the retention gap into the gas chromatograph column.

8. The method of claim 5 wherein in step (d) at least nine-tenths of the stream of carrier gas emerging from the retention gap enriched with the volatile solvent of the injected sample is flowed to waste for a first period of time, the first period of time being less than the period of time needed to transport more than one-quarter of the component of interest of the injected sample through the retention gap and being greater than the period of time needed to transport three-quarters of the solvent of the injected sample through the retention gap and wherein in step (e) at least nine-tenths of the stream of carrier gas emerging from the retention gap is flowed into the gas chromatography column for a second period of time needed to transport at least two-thirds of the component of interest of the injected sample from the retention gap into the gas chromatography column.

9. The method of claim 1 wherein in step (b) the atmospheric pressure boiling point of the component of interest is less than 25° C. higher than the atmospheric pressure boiling point of the solvent.

10. The method of claim 9 wherein in step (d) at least three quarters of the stream of carrier gas emerging from the retention gap enriched with the volatile solvent of the injected sample is flowed to waste for a first period of time, the first period of time being less than the period of time needed to transport more than one-half of the component of interest of the injected sample through the retention gap and being greater than the period of time needed to transport one-half of the solvent of the injected sample through the retention gap and wherein in step (e) at least one-half of the stream of carrier gas emerging from the retention gap is flowed into the gas chromatography column for a second period of time needed to transport at least one-quarter of the component of interest of the injected sample from the retention gap into the gas chromatography column.

11. The method of claim 9 wherein in step (d) at least nine-tenths of the steam of carrier gas emerging from the retention gap enriched with the volatile solvent of the injected sample is flowed to waste for a first period of time, the first period of time being less than the period of time needed to transport more than one-half of the component of interest of the injected sample through the retention gap and being greater than the period of time needed to transport one-half of the solvent of the injected sample through the retention gap and wherein in step (e) at least three-quarters of the stream of carrier gas emerging from the retention gap is flowed into the gas chromatography column for a second period of time needed to transport at least one-third of the component of interest of the injected sample from the retention gap into the gas chromatography column.

12. The method of claim 9 wherein in step (d) at least nine-tenths of the stream of carrier gas emerging from the retention gap enriched with the volatile solvent of the injected sample is flowed to waste for a first period of time, the first period of time being less than the period of time needed to transport more than one-quarter of the component of interest of the injected sample through the retention gap and being greater than the period of time needed to transport three-quarters of the solvent of the injected sample through the retention gap and wherein in step (e) at least nine-tenths of the stream of carrier gas emerging from the retention gap is flowed into the gas chromatography column for a second period of time needed to transport at least two-thirds of the component of interest of the injected sample from the retention gap into the gas chromatography column.

* * * * *

UNITED STATES PATENT AND TRADEMARK OFFICE
CERTIFICATE OF CORRECTION

PATENT NO. : 5,001,071

DATED : Mar. 19, 1991

INVENTOR(S) : Paul L. Morabito; Joseph F. Hiller; Terrence McCabe; Thomas L. Peters It is certified that error appears in the above-identified patent and that said Letters Patent is hereby corrected as shown below:

Column 6:
Claim 1, line 25, step (e), after "of", second occurrence, insert --carrier gas emerging from the retention gap into a--.

Signed and Sealed this

Eighth Day of December, 1992

Attest:

DOUGLAS B. COMER

Attesting Officer

Acting Commissioner of Patents and Trademarks